US005856598A

United States Patent [19]

Berger et al.

[11] Patent Number: 5,856,598

[45] Date of Patent: Jan. 5, 1999

[54] DIELECTRIC COMPOSITION BASED ON POLYARYLALKANES WHICH HAVE IMPROVED DIELECTRIC PROPERTIES

[75] Inventors: Noëlle Berger, Ecully; Raymond Commandeur, Vizille, both of France

[73] Assignee: Elf Atochem S.A., France

[21] Appl. No.: 537,394

[22] Filed: Oct. 2, 1995

[30] Foreign Application Priority Data

Sep. 30, 1994 [FR] France .................................. 94 11718

[51] Int. Cl.[6] ............................ H01B 3/22; C07C 15/00

[52] U.S. Cl. ............................................... 585/6.3; 585/25

[58] Field of Search ....................................... 585/25, 6.3

[56] References Cited

U.S. PATENT DOCUMENTS

| | | | |
|---|---|---|---|
| 4,523,044 | 6/1985 | Commanduer et al. | 585/25 |
| 4,621,302 | 11/1986 | Sato et al. | 585/6.3 |
| 4,639,833 | 1/1987 | Sato et al. | 585/6.3 |
| 4,642,730 | 2/1987 | Sato et al. | 585/25 |
| 4,734,824 | 3/1988 | Sato et al. | 585/6.3 |
| 4,753,745 | 6/1988 | Kostusyk et al. | 585/25 |
| 4,956,120 | 9/1990 | Commandeur et al. | 585/25 |
| 4,957,815 | 9/1990 | Commandeur et al. | 585/25 |
| 5,384,058 | 1/1995 | Commandeur et al. | 585/25 |
| 5,446,228 | 8/1995 | Commandeur et al. | 585/25 |
| 5,545,355 | 8/1996 | Commandeur et al. | 585/25 |
| 5,593,613 | 1/1997 | Commandeur et al. | 585/25 |
| 5,601,755 | 2/1997 | Commandeur et al. | 585/25 |

FOREIGN PATENT DOCUMENTS

| | | |
|---|---|---|
| 0 154 993 | 9/1985 | European Pat. Off. . |
| 0 172 537 | 2/1986 | European Pat. Off. . |

OTHER PUBLICATIONS

Chemical Abstracts, Abstract No. 138427c, vol. 80, No. 24, Jun. 17, 1974.

*Primary Examiner*—Ellen M. McAvoy
*Attorney, Agent, or Firm*—Millen, White, Zelano & Branigan, P.C.

[57] ABSTRACT

The invention relates to a dielectric composition including at least one polyarylalkane oligomer of formula:

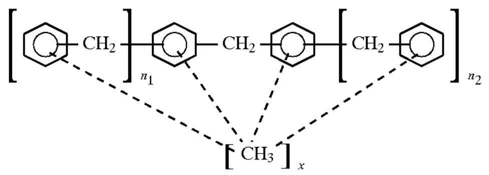

(I)

in which $n_1$ and $n_2$=0, 1 or 2, with the proviso that $n_1+n_2=1$ or 2, x=0, 1, 2, 3, 4, 5 or 6 and that the said composition has, in particular, a breakdown voltage increasing with the temperature.

15 Claims, 7 Drawing Sheets

DIELECTRIC COMPOSITION BASED ON POLYARYLALKANES WHICH HAVE IMPROVED DIELECTRIC PROPERTIES

BACKGROUND OF THE INVENTION

The present invention relates to a dielectric composition based on polyarylalkanes which has improved dielectric properties and to its use in electrical equipment operating at high temperature, especially distribution transformers.

A trend nowadays is to employ distribution transformers in respect of which attempts are made to increase the power while maintaining the same dimensions.

This increase in power per unit volume results in an increase in the operating temperatures, which may run from 60° C. –80° C. in the case of conventional transformers, to 150° C. or 200° C. in the case of so-called "high temperature" distribution transformers.

For this new type of equipment, liquids are being sought which have good dielectric properties even at high temperature, a good heat stability, as well as low vapor pressure and a viscosity that is sufficiently low for removing the thermal energy.

The insulating oils commonly employed, such as mineral oils, silicone oils and pentaerythritol esters have a relatively mediocre high-temperature behaviour. In the case of silicone oils in particular, a lowering of the breakdown voltage was observed when the temperature rose (study performed by General Electric Co. for the U.S. Department of Energy—report HCP/T-2115 published in February 1979—FIG. 3.3, page 35) .

This behaviour appears to be general, because it has also been observed in synthetic liquids such as hexane (IEEE Trans. Electr. Insul. vol. E1–13, No. 4, August 1978, p. 263) and in mineral oils ("Insulating Materials for Design and Practice" by Franck M. Clark, page 151—Publ. John Wiley and Soils, Inc.).

This introduces in particular the disadvantage of not being able to keep the same distances between the conductors if it is desired to increase the power of the equipment and, consequently, results in an increase in its size.

Furthermore, mineral oils and silicone oils exhibit limited heat stabilities.

In addition, silicone oils are poor heat transfer agents.

SUMMARY OF THE INVENTION

A composition has now been found which has better dielectric properties, in particular a breakdown voltage which increases with the temperature, a good heat stability, a low vapor pressure, and which is also a good heat transfer agent.

The composition according to the invention is characterized in that it includes at least one polyarylalkane oligomer which consists of an isomer or a mixture of isomers of formula:

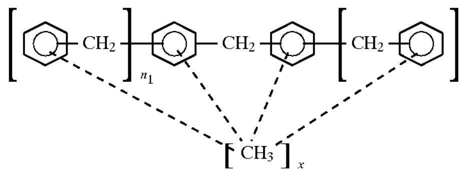

(I)

in which $n_1$ and $n_2$=0, 1 or 2, with the proviso that $n_1+n_2$ is equal to 1 or 2 x=0, 1, 2, 3, 4, 5 or 6 and that the said composition has a) a vapor pressure not exceeding 1 torr at 150° C. and, preferably, not exceeding 0.25 torr, b) a thermal quality coefficient, defined as the product of the specific heat at 100° C. (J/1/°C.) and of the thermal conductivity at 100° C. (W/m/°C.), divided by the viscosity at 100° C. ($mm^2$/s) and multiplied by 100, of at least 3 and, preferably, at least 6, c) a rate of formation of volatiles at 260° C. during 500 hours not exceeding 3 g/kg and, preferably, not exceeding 1 g/kg, d) a breakdown voltage at 20° C. of at least 60 kV and, preferably, at least 80 kV, and at 80° C. of at least 110 kV and, preferably, at least 130 kV, measured in 50 Hz alternating current in a cell equipped with an electrode consisting of a rod of 0.6 mm diameter and with an electrode consisting of a Rogowski disc with a rounded edge 40 mm in diameter, the said electrodes being separated by a distance of 40 mm.

By way of illustration of an oligomer of formula (I) forming part of the composition according to the invention there may be mentioned;

the oligomer of formula (I) in which $n_1$=1, $n_2$=0 and x=1

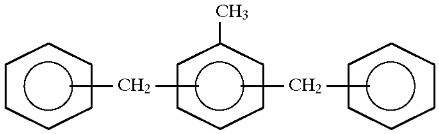

(Ia)

the oligomer of formula (I) in which $n_1$=0, $n_2$=1 and x–1

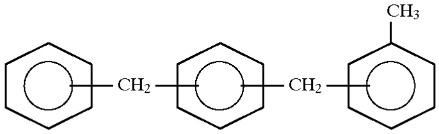

(Ib)

the oligomer of formula (I) in which $n_1$ and $n_2$=0, 1 or 2, it being known that $n_1+n_2$=2 and x=1.

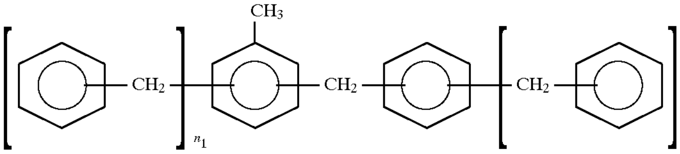

(Ic)

According to the present invention it is preferred to employ a composition including a weight quantity of oligomers (Ia) and (Ib) of at least 40% and, preferably, a weight quantity ranging from 70% to more than 99% and a weight quantity of oligomers (Ic) of less than 3% and, preferably, a weight quantity ranging from 0.5% to 2%.

The composition of the present invention may optionally contain very small quantities of polyarylalkane oligomers of formula (I) in which $n_1$=$n_2$=0 and x=1 (benzyltoluenes) or even of the polyarylalkane oligomers of formula (I) in which $n_1=n_2=0$ and x=0 (benzylbenzene).

It is desirable that the weight quantity of benzyltoluenes and benzylbenzenes in the composition should be as low an possible, or even virtually nil, because their presence is liable to increase especially the vapor pressure of the said composition, which rules them out for the use envisaged.

These compounds also have the disadvantage of considerably lowering the flash and fire points of the compositions containing them. This rules them out when these compositions must be employed in high-temperature distribution transformers. it would not constitute & departure from the scope of the invention if the polyarylalkane oligomer of formula (I) was accompanied by at least one polyarylalkane oligomer consisting of an isomer or mixture of isomers of formula

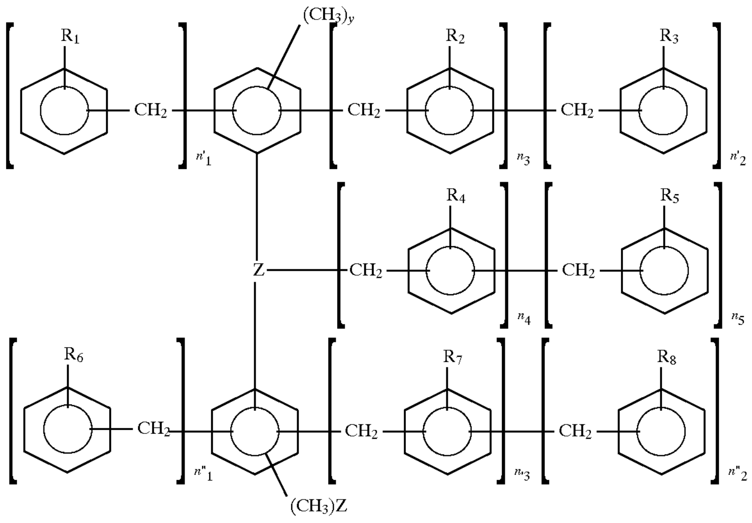

(II)

in which Z is a trivalent connecting group such as:

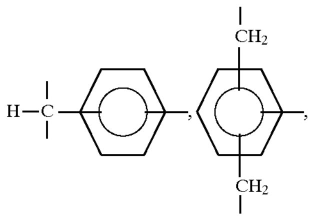

$R_1$, $R_2$, $R_3$, $R_4$, $R_5$, $R_6$, $R_7$ and $R_8$ are identical or different and denote H or $CH_3$, $n'_1$, $n''_1$ and $n_4$=0, 1 or 2, $n'_2$, $n''_2$, $n_3$, $n'_3$ and $n_5$=0 or 1, $n'_1+n''_1+n'_2+n''_2+n_3+n'_3+n_4+n_5 \leqq 2$, y and z=0, 1 or 2.

By way of illustration of oligomers of formula (II) there may be mentioned the ditolylphenylmethanes:

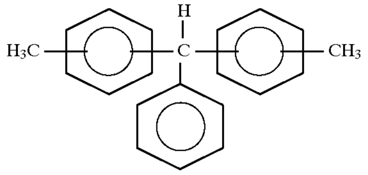

(IIa)

According to the present invention the composition may include a weight quantity of oligomers of formula (II) which does not exceed 10%.

According to a preferred form of the invention the composition may include:

60% to 70% by weight of oligomers (I*a*),

20% to 30% by weight of oligomers (I*b*),

0% to 2% by weight of oligomers (I*c*),

0% to 10% by weight of ditolylphenylmethanes (II*a*), the total being equal to 100%.

The various products or isomers of the composition according to the invention, that is to say the polyarylalkane oligomers of formula (I) and (II), may be prepared by condensation of benzyl or methylbenzyl chloride containing a variable quantity of benzylidene chloride with toluene or xylene or the mixture of the two in the presence of a Friedel and Crafts catalyst.

In practice the condensation takes place at a temperature of between 50° C. and 150° C.

The quantity of catalyst is generally between 50 ppm and 1% by weight of the reaction mass.

Metal halides such as ferric chloride, aluminium chloride, antimony trichloride and titanium tetrachloride may be employed as the Friedel and Crafts catalyst.

The reaction mixture obtained consists essentially of polyarylalkane oligomers of formula (I) and (II) and of unreacted toluene.

The reaction mixture may undergo a dechlorination treatment. For this purpose it is possible to employ the process described in EP 306398 employing an alkali metal alcoholate or else the process described in EP 225849 employing sodium metal, the content of these applications being incorporated in the present invention.

After the dechlorination treatment a simple distillation is performed, generally at reduced pressure, in order to recover the oligomers of formula (I) and, optionally, (II).

The volatiles such as benzyltoluenes and benzylbenzene are advantageously removed in a first distillation, at the same time as the unreacted toluene or xylene, and are recycled before the dechlorination treatment.

A heavy fraction is obtained at the bottom which may contain the residues of the dechlorinating agent, NaCl, catalyst residues and heavier polyarylalkane oligomers of formula (I) and/or (II), such as, for example, the compounds of formula (I) in which $n_1+n_2=2$.

The products obtained may be purified by a technique which consists in using a fuller's earth or activated alumina, either by itself or as a mixture according to the specific techniques which are known in the dielectric liquids sector.

Similarly, it may be advantageous to add stabilizers of the epoxide type or of other kind, such as, for example, tetraphenyltin, or antioxidants.

These adjuvants are generally added in quantities which may vary between 0.001% and 10%, preferably between 0.01% and 0.3%.

The compositions of the invention are advantageously employed as dielectric liquids for insulation operating at high temperature, such as, for example, in transformers with improved power per unit volume.

They exhibit, in fact, the advantage of having a breakdown voltage which increases with the temperature, in contrast to the liquids commonly employed, such as mineral oils, silicone oils or alkylbenzenes.

These compositions according to the invention furthermore have a better resistance to partial discharges. In addition, they exhibit a much better heat stability.

The compositions according to the invention also offer the advantage of having flash points and fire points higher than 200° C., which is the maximum temperature of use.

DETAILED DISCUSSION OF FIGURES

All of the figures are discussed in the following Example.

The examples which follow illustrate the invention.

EXAMPLE 1

40 moles of toluene are charged into a reactor fitted with a stirrer, a condenser, a chlorine food tube and a 30-watt Philips TLADK lamp. 10 moles of gaseous chlorine are introduced over 4 hours at the temperature of 90° C. The reaction mixture is degassed, cooled and then introduced gradually into a reactor containing 4 moles of toluene and 1 g of ferric chloride at the temperature of 90° C. At the end of reaction the reaction mass is degassed and then subjected to a distillation with a four-plate column at a reduced pressure of 100 mm of mercury so as to remove the unconverted toluene.

The pressure is then lowered to about 10 mm of mercury so as to remove the benzyltoluene isomers.

The vapor temperature is 140° C./150° C. The temperature at the bottom increases to 240° C. The mixture of oligomers obtained at the bottom consists of oligomers of formula (I) in which $n_1+n_2\geqq 1$ with x=1, and the oligomers of formula (II).

This mixture is treated with 2% of sodium methylate for 6 hours at 300° C. under a stream of nitrogen and is then subjected to a distillation at a reduced pressure of 3 mm of mercury with a 4-plate column.

The fraction which comes over between 200° C. –210° C. has the following weight composition:

92.9% of (I*a*) and (I*b*)

4.1% of oligomers of formula (II) in which

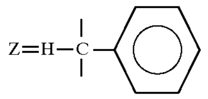

$$n'_1+n''_1+n'_2+n''_2+n_3+n'_3+n_4+n_4=0$$

and y=z=1

(ditolylphenylmethanes)

1.9% of (I*c*)

less than 1% of benzyltoluenes (formula (I) in which $n_1+n_2=0$ and x=1).

The composition obtained is the one which will be employed in all the tests which are to follow.

Test for determining the breakdown voltages.

Figure 1:
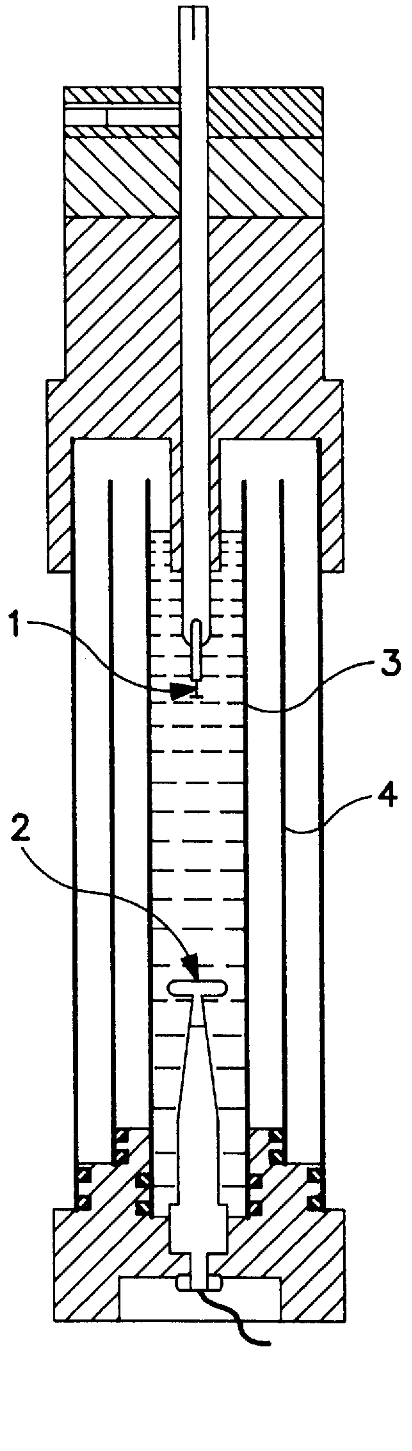
FIG. 1 is a vertical schematic section of a test cell for determining breakdown voltages.

The measurements were performed in 50 Hz alternating current in a divergent field (0.6 mm point) in a cell as illustrated in FIG. 1 the electrodes being:

a rod of 0.6 mm diameter (1)

a rounded-edge Rogowski disc 40 mm in diameter (2) and having two volumes:

a volume of 0.7 liters (3), a volume of 3 liters (4).

5 to 6 measurements of the breakdown voltage were carried out for each separation between the electrodes by applying a voltage gradient of 3000 V/s.

Figure 3:
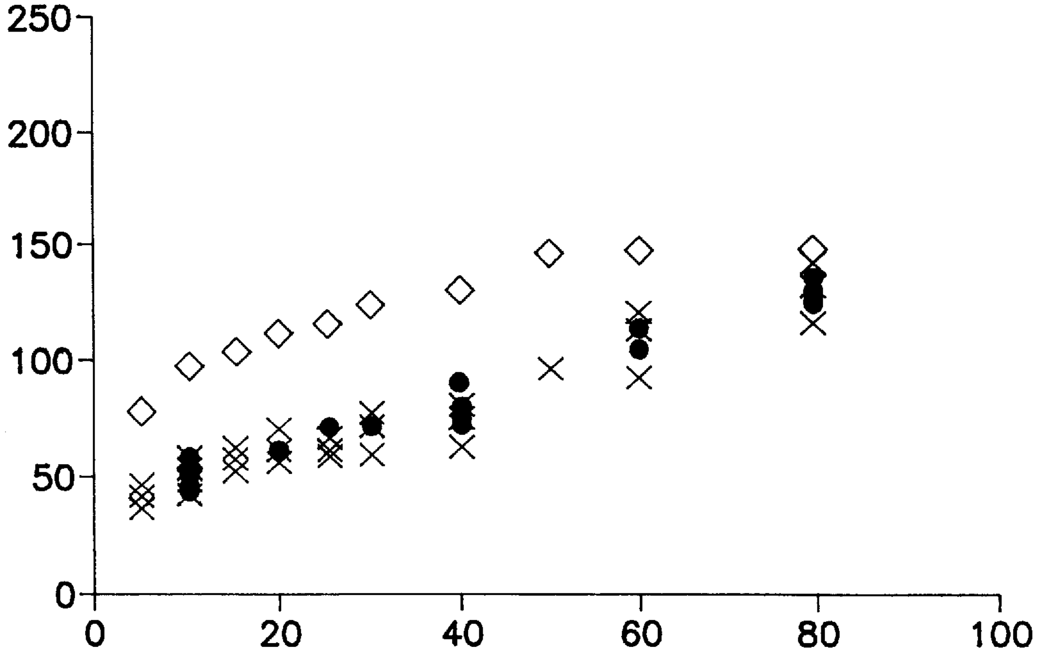
FIG. 3 is a graph of a series of tests to determine breakdown voltage measurements at 20° C.

In a first series of tests we performed breakdown voltage measurements at ambient temperature (20° C.), on the one hand on the composition of Example 1, on the other hand on various mineral oils and on dodecylbenzene. The results are plotted in the graph of FIG. 3. In this graph we have shown the breakdown voltage in kV as ordinate and the distance between the electrodes in mm as abscissa.

Also shown in this graph are:

● represent the composition according to Example 1,

◇ represent dodecylbenzene, x represent the paraffinic oil called Univolt 52,

+ represent the naphthenic mineral oil called Nytro 10 G.

It can be seen in this graph that the composition according to Example 1 exhibits systematically a breakdown voltage equal to that of the mineral oil, which increases when the separation between the electrodes increases, in contrast to dodecylbenzene (◇), the breakdown voltage of which is seen to reach a ceiling starting from a certain separation.

In a second series of tests we performed breakdown voltage measurements at between 20° C. and 80° C., on the one hand on the composition of Example 1, on the other hand on dodecylbenzene and on the naphthenic mineral oil Nytro 10 G.

Figure 4:
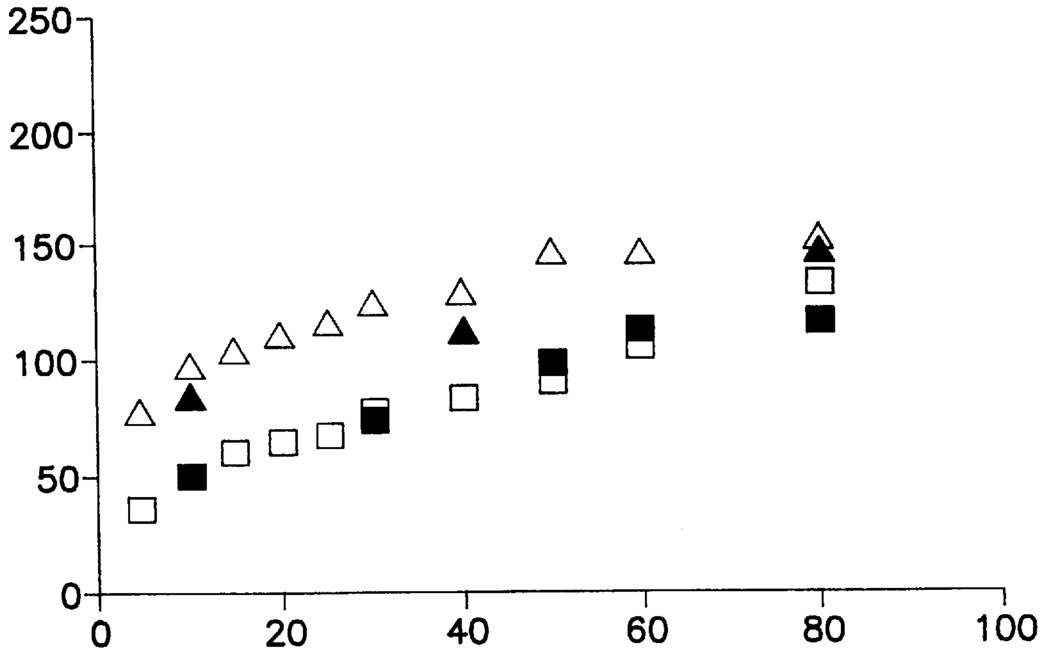
FIGS. 4 and 5 are directed to a second series of tests performed at between 20° C. and 80° C., FIG. 4 being directed to the composition of Example 1 and FIG. 5 being directed to compositions not in accordance with the invention.
Figure 5:
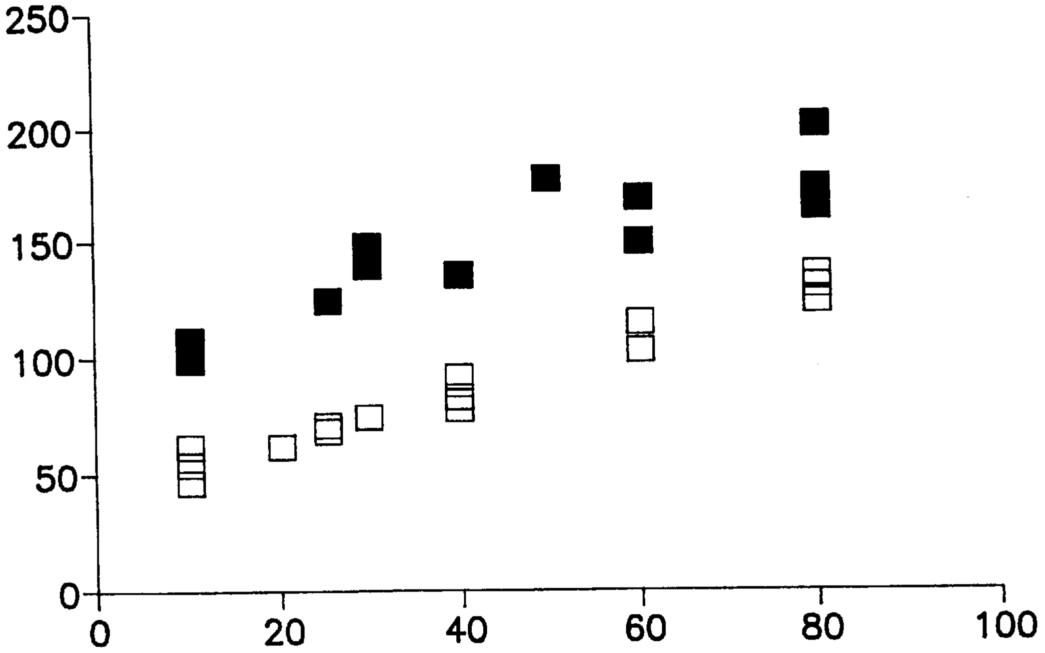

The results are plotted in the graphs of FIGS. 4 and 5.

In these graphs we have shown:

the breakdown voltage in kV as ordinate the distance between the electrodes in mm as abscissa.

In the graph of FIG. 4 are shown tests not in accordance with the invention, wherein:

| | |
|---|---|
| Δ represent tests at 20° C. | } in the case of |
| ▲ represent tests at 80° C. | } dodecylbenzene |
| □ represent tests at 20° C. | } in the case of the naphthenic mineral |
| ■ represent tests at 80° C. | } oil Nytro 10 G |

It can be seen in the graph of FIG. 4 that there is no difference in breakdown voltage between 20° C. and 80° C. in accordance with what is known.

In the graph of FIG. 5 are shown (tests according to the invention wherein:

| | |
|---|---|
| □ represent tests at 20° C. | } on the composition |
| ■ represent tests at 80° C. | } of Example 1 |

An increase in the breakdown voltage with the temperature is observed whatever the separation between the electrodes. For example, in the case of a separation between the electrodes of 40 mm there is a breakdown voltage of 80 kV at 20° C. and of 130 kV at 80° C.

Test for determining the vapor pressure

This was carried out according to a method described in:

Fluid Phase Equlibria, 42, pages 287 to 304 (1988).

In the case of the composition of Example 1, it was found to be equal to 0.244 mm Hg at 150.9° C.

Test for determining the volatiles at 260° C. (heat stability tests)

Figure 2:
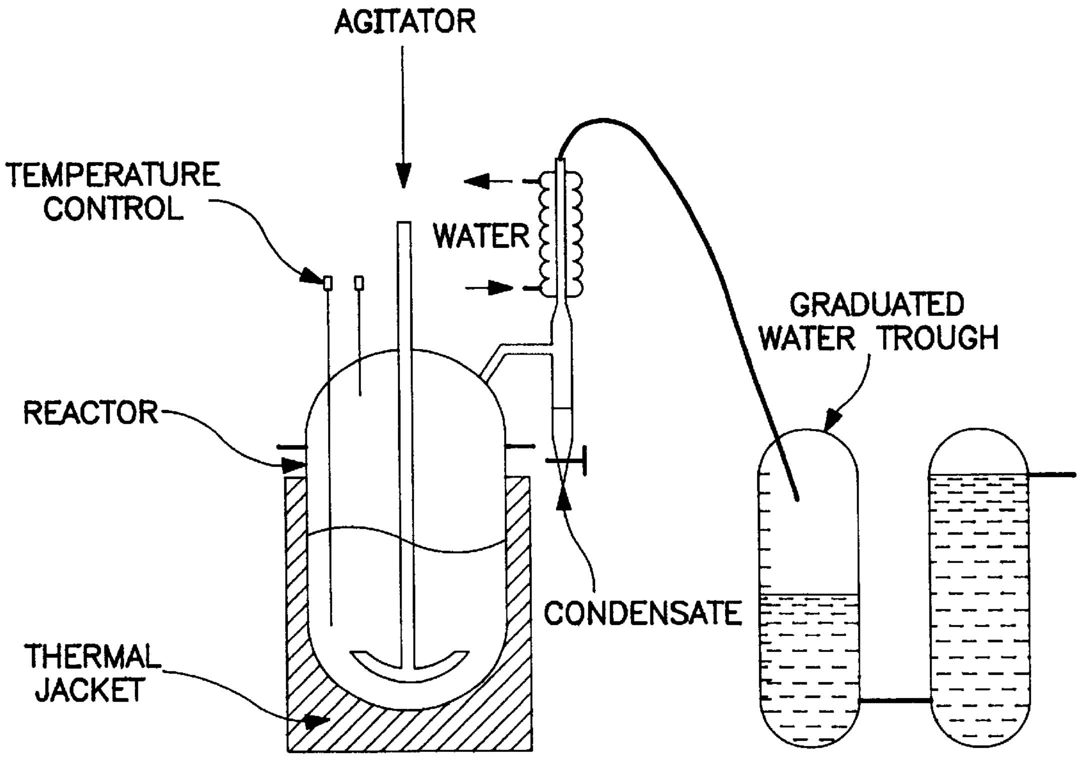
FIG. 2 is a schematic representation of apparatus for determining the content of volatile products.

The test was carried out in an apparatus as illustrated in FIG. 2.

The test conditions are the following:

test period: 500 hours temperature: 260° C.

the condensable decomposition products are recovered in a water condenser and the noncondensable decomposition products are trapped in a water trough.

Figure 6:
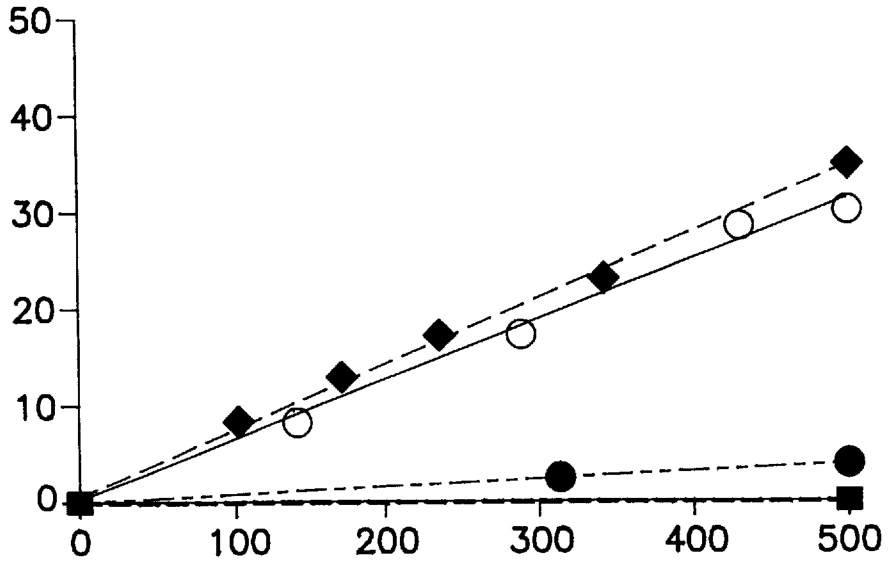
FIGS. 6 and 7 are graphs indicating the release of condensable volatile products at temperatures from 0° to 500° C., FIG. 6 being in g/kg and FIG. 7 in l/kg.
Figure 7:
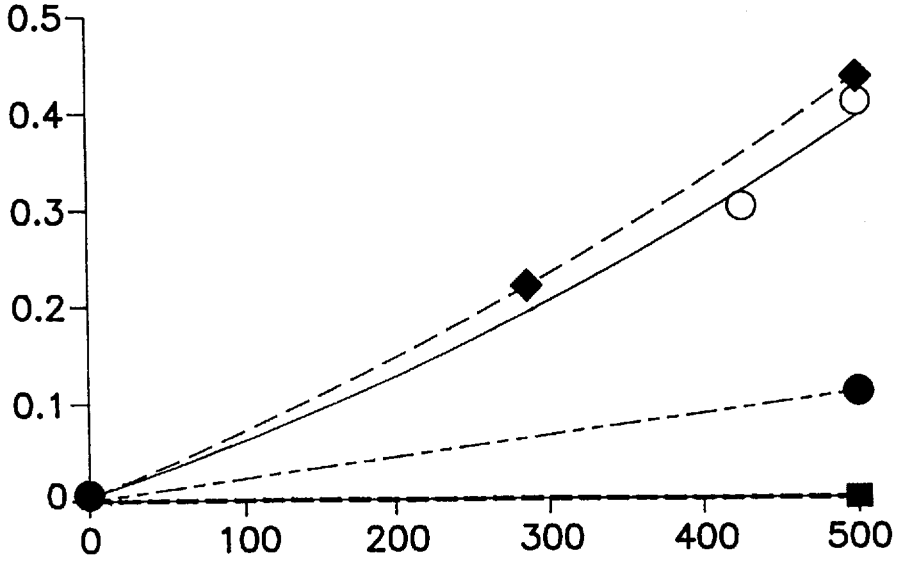

The thermal decomposition is followed with time. The results are plotted in the graphs of FIG. 6 and 7. In these graphs we have shown the release of condensable volatile products, in g/kg (FIG. 6) and in liters/kg (FIG. 7), as ordinate and the time in hours as abscissa, wherein:

● represent the paraffinic oil UNIVOLT 52,

■ represent the composition of Example 1,

♦ represent a silicone oil employed in transformers,

○ a pentaerythritol ester called MIDEL.

It is found that the rate of formation of condensable and noncondensable volatile products is virtually nil at 260° C. after 500 hours.

Test for determining the thermal quality coefficient

The specific heat is determined at 100° C. by calorimetry.

The thermal conductivity is determined at 100° C. according to ASTM D 2717.

The viscosity is determined at 100° C. according to ASTM D 445.

The following relationship is then applied:

$$\frac{\text{specific heat} \times \text{thermal conductivity}}{\text{viscosity}} \times 100$$

In the case of the composition of Example 1, the details are:

specific heat at 100° C. =1.802 J/l/°C.

thermal conductivity at 100° C. =0.12146 W/m/°C.

viscosity at 100° C. =3.1 $mm^2/s$

The thermal quality coefficient is therefore $$\text{equal to: } \frac{1.802 \times 0.12146}{3.1} \times 100 = 7.06$$

The preceding examples can be repeated with similar success by substituting the generically or specifically described reactants and/or operating conditions of this invention for those used in the preceding examples.

The entire disclosures of all applications, patents and publications, cited above and below, and of corresponding French application 94/11718, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. In an electrical distribution high temperature power transformer, the improvement wherein said power transformer contains an insulating oil consisting essentially of a dielectric composition comprising at least one polyarylalkane oligomer which consists essentially of an isomer or an isomeric mixture of the formula:

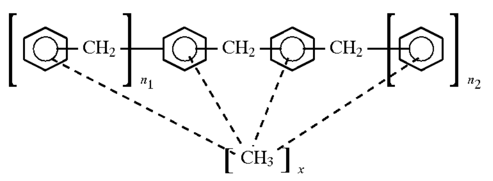

(I)

in which $n_1$ and $n_2$=0, 1 or 2, with the proviso that $n_1+n_2$ is equal to 1 or 2, x=0, 1, 2, 3, 4, 5 or 6 and that the said composition has a) a vapor pressure not exceeding 1 torr at 150° C., b) a thermal quality coefficient, defined as the product of the specific heat at 100° (J/l/°C.) and of the thermal conductivity at 100° C. (W/m/°C.), divided by the viscosity at 100° C. ($mm^2/s$) and multiplied by 100, of at least 3, c) a rate of formation of volatiles at 260° C. during 500 hours not exceeding 3 g/kg, d) a breakdown voltage at 20° C. of at least 60 kV and at 80° C. of at least 110 kV, measured in 50 Hz alternating current in a cell equipped with an electrode consisting of a rod of 0.6 mm diameter and with an electrode consisting of a Rogowski disc with a rounded edge 40 mm in diameter, the said electrodes being separated by a distance of 40 mm.

2. A power transformer according to claim 1, said composition having:

a) a vapor pressure not exceeding 0.25 torr at 150° C., b) a thermal quality coefficient of at least 6, c) a rate of formation of volatiles at 260° C. during 500 hours not exceeding 1 g/kg, and d) a breakdown voltage at 20° C. of at least 80 kV and at 80° C. of at least 130 kV.

3. A power transformer according to claim 1 said composition including, it includes a weight quantity of oligomers (I*a*)—oligomers of formula (I) in which $n_1=1$, $n_2=0$ and x=1—and of oligomers (I*b*) —oligomers of formula (I) in which $n_1$0, $n_2=1$ and x=1—of at least 40% and a weight quantity of oligomers (I*c*)—oligomers of formula (I) in which $n_1$ and $n_2=0$, 1 or 2, it being known that $n_1+n_2=2$ and x=1—not exceeding 3%.

4. A power transformer according to claim 3, said composition including a weight quantity of oligomers (I*a*) and (I*b*) ranging from 70% to more than 99% and a weight quantity of oligomers (I*c*) ranging from 0.5% to 2%.

5. A power transformer according to claim 1, further including at least one polyarylalkane oligomer which consists essentially of an isomer or mixture of isomers of formula:

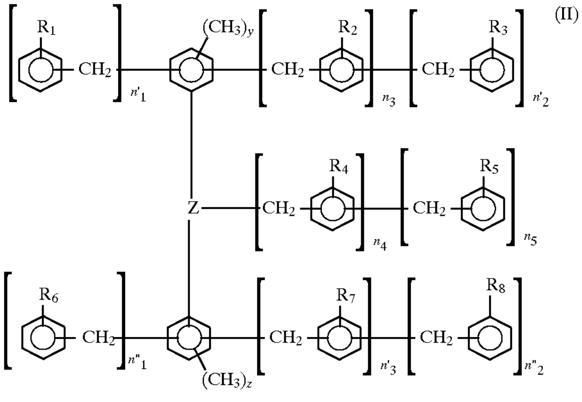
(II)

in which Z is a trivalent connecting group such as:

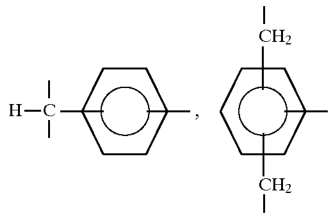

$R_1$, $R_2$, $R_3$, $R_4$, $R_5$, $R_6$, $R_7$, and $R_8$ are identical or different and denote H or $CH_3$, $n'_1$, $n''_1$ and $n_4=0$, 1 or 2, $n'_2$, $n''_2$, $n_3$, $n'_3$ and $n_5=0$ or 2, $n'_1+n''_1+n'_2+n''_2+n_3+n'_3+n_4+n_5 \leqq 2$, y and z=0, 1 or 2.

6. A power transformer according to claim 5, wherein the oligomers of formula (II) are ditolylphenylmethanes of the formula:

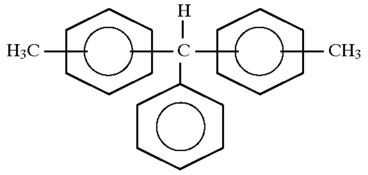
(IIa)

7. In an electrical distribution power transformer, the improvement wherein said power transformer contains an insulating oil consisting essentially of a dielectric composition according to claim 1.

8. A power transformer according to claim 3, said composition comprising:

60% to 70% by weight of oligomers (I*a*),

20% to 30% by weight of oligomers (I*b*),

0% to 10% by weight of ditolylphenylmethanes (II*a*), the total being equal to 100%.

9. A power transformer according to claim 1, wherein said composition comprises at least 60% by weight of said isomer or isomeric mixture.

10. A dielectric composition comprising at least 60% by weight of at least one polyarylalkane oligomer which consists essentially an isomer or an isomeric mixture of the formula:

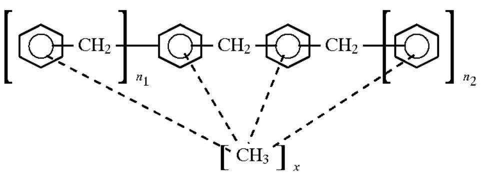
(I)

in which $n_1$ and $n_2=0$, 1 or 2, with the proviso that $n_1+n_2$ is equal to 1 or 2, x=0, 1, 2, 3, 4, 5 or 6 and that the said composition has a) a vapor pressure not exceeding 1 torr at 150° C., b) a thermal quality coefficient, defined as the product of the specific heat at 100° (J/l/°C.) and of the thermal conductivity at 100° C. (W/m/°C.), divided by the viscosity at 100° C. ($mm^2/s$) and multiplied by 100, of at least 3, c) a rate of formation of volatiles at 260° C. during 500 hours not exceeding 3 g/kg, d) a breakdown voltage at 20° C. of at least 60 kV and at 80° C. of at least 110 kV, measured in 50 Hz alternating current in a cell equipped with an electrode consisting of a rod of 0.6 mm diameter and with an electrode consisting of a Rogowski disc with a rounded edge 40 mm in diameter, the said electrodes being separated by a distance of 40 mm.

11. A composition according to claim 10, said composition including a weight quantity of oligomers (I*a*)—oligomers of formula (I) in which $n_1=1$, $n_2=0$ and x=1—and of oligomers (I*b*)—oligomers of formula (I) in which $n_1=0$, $n_2=1$ and x=1—of at least 60% and a weight quantity of oligomers (I*c*)—oligomers of formula (I) in which $n_1+n_2=2$ and x=1—not exceeding 3%.

12. A composition according to claim 11, said composition including a weight quantity of oligomers (I*a*) and (I*b*) ranging from 70% to more than 99% and a weight quantity of oligomers (I*c*) ranging from 0.5% to 2%.

13. A composition according to claim 11, additionally including at least one polyarylalkane oligomer which consists essentially of a mixture of isomers of the formula:

(II)

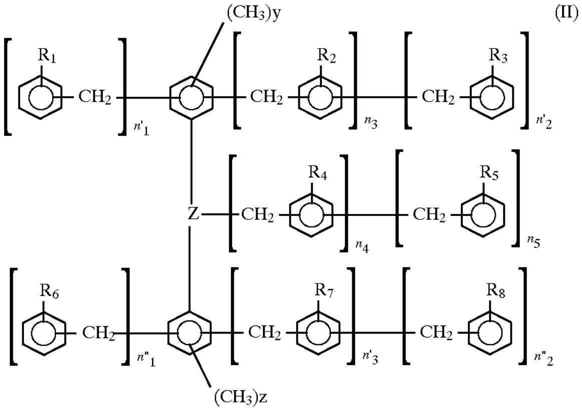

in which Z is a trivalent connecting group such as:

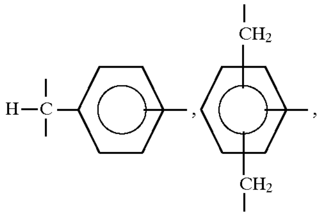

$R_1$, $R_2$, $R_3$, $R_4$, $R_5$, $R_6$, $R_7$ and $R_8$ are identical or different and denote H or $CH_3$, $n'_1$, $n''_1$ and $n_4$=0, 1 or 2, $n'_2$, $n''_2$, $n_3$, $n'_3$ and $n_5$ is 0 or 1, $n'_1+n''_1+n'_2+n''_2+n_3+n'_3+n_4+n_5 \leq 2$, y and z=0, 1 or 2.

14. A composition according to claim 13, wherein the oligomers of formula (II) are ditolylphenylmethanes of the formula:

(IIa)

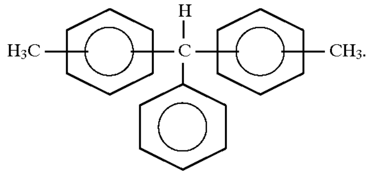

15. A composition according to claim 14, wherein the composition comprises:

60% to 70% by weight of oligomers (I*a*),

20% to 30% by weight of oligomers (I*b*), above 0% to 10% by weight of ditolylphenylmethanes (II*a*), the total being equal to 100%.

* * * * *